United States Patent [19]

Kuroiwa et al.

[11] Patent Number: 4,861,713
[45] Date of Patent: Aug. 29, 1989

[54] NOVEL METHOD FOR DETERMINING CHOLINESTERASE ACTIVITY

[75] Inventors: Katsumasa Kuroiwa; Katsuhiro Katayama, both of Koriyama; Takeshi Nagasawa, Urawa, all of Japan

[73] Assignee: Nitto Boseki Co., Ltd., Fukushima, Japan

[21] Appl. No.: 38,293

[22] Filed: Apr. 14, 1987

[30] Foreign Application Priority Data

Apr. 15, 1986 [JP] Japan ............................. 61-86744

[51] Int. Cl.$^4$ .............................................. C12Q 1/46
[52] U.S. Cl. ........................................ 435/20; 560/70
[58] Field of Search ............................ 435/20; 560/70

[56] References Cited

U.S. PATENT DOCUMENTS 4,565,780 1/1986 Motonaga et al. .................. 435/20
4,717,659 1/1988 Kuroiwa ............................... 435/20

FOREIGN PATENT DOCUMENTS 0160980 11/1985 European Pat. Off. .............. 435/20
2018988 10/1979 United Kingdom .

OTHER PUBLICATIONS

Journal of Chromatography, vol. 260, 1983, pp. 193-199, S. Clausen et al., "Separation of Aromatic Choline Esters by High-Performance Liquid Chromatography".

Primary Examiner—Robert J. Warden
Assistant Examiner—Robert Benson
Attorney, Agent, or Firm—Bert J. Lewen; Henry Sternberg

[57] ABSTRACT

This invention relates to a method for determination of cholinesterase activity, characterized by using, as a substrate, a choline derivative represented by the general formula (I):

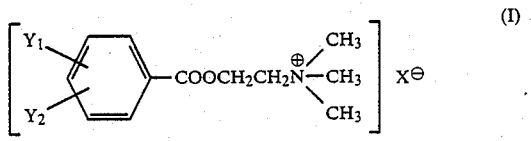

wherein X is a halogen atom; $Y_1$ is a hydroxyl group as a substituent in the 2- or 5-position; and $Y_2$ is a hydroxyl group as a substituent in the 3-position.

The determination method of this invention permits easy and simple determination of cholinesterase activity, and is very useful as a determination method for clinical examinations for the purpose of determining cholinesterase in serum.

6 Claims, 10 Drawing Sheets (a) 2,3-DIHYDROXYBENZOYLCOLINE IODINE
(b) 2,3-DIHYDROXYBENZOIC ACID (a) 3,5-DIHYDROXYBENZOYL COLINE IODINE
(b) 3,5-DIHYDROXYBENZOIC ACID

NOVEL METHOD FOR DETERMINING CHOLINESTERASE ACTIVITY

FIELD OF THE INVENTION

This invention relates to a method for determination of cholinesterase activity in serum in clinical examinations. More particularly, this invention relates to a method for determination of cholinesterase activity, characterized by using, as a substrate, a choline derivative represented by the general formula (I):

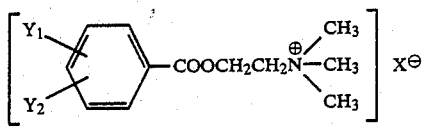

wherein X is a halogen atom; $Y_1$ is a hydroxyl group as a substituent in the 2- or 5-position; and $Y_2$ is a hydroxyl group as a substituent in the 3-position.

The determination method of this invention permits easy and simple determination of cholinesterase activity, and is very useful as a determination method for clinical examinations for the purpose of determining cholinesterase activity in serum.

BACKGROUND OF THE INVENTION

In general, the concentration of cholinesterase in serum is known to be decreased, for example, in a patient with liver disease, while it is known to be increased, for example, in a patient with kidney disease. Therefore, these diseases can be diagnosed by determining the cholinesterase activity in serum of these patients and a determination method which permits exact determination of cholinesterase activity in serum can be used for clinical examinations.

As methods for determining cholinesterase (hereinafter referred to as ChE) activity in serum, there have heretofore been reported various methods using a synthetic substrate, and some of them have been made practicable for daily clinical examinations. However, these determination methods involve various defects and problems, and these disadvantages are responsible for the inaccuracy of the resulting determined value. Examples of the heretofore well-known determination methods include (a) gas analysis method, (b) pH meter method, (c) pH-indicator colorimetric method, (d) thiocholine color formation method, (e) enzymatic method, (f) UV method, etc.

(a) The gas analysis method [R. Ammon: Pflügers Arch. Ges Physiol., 233, 487 (1933)] comprises using acetylcholine as a synthetic substrate, bringing acetic acid produced by the enzymatic action of ChE into contact with sodium hydrogen carbonate, and quantitatively determining the carbon dioxide gas produced. This method, however, is disadvantageous, for example, in that since its operations are troublesome, it cannot deal with many samples.

(b) The pH meter method [H. O. Michel: J. Lab. & Clin. Med., 34, 1564 (1949)], like the gas analysis method, comprises using acetylcholine as a synthetic substrate, and measuring a pH change due to acetic acid produced by the enzymatic action of ChE by means of a pH meter. This method, however, involves a problem of low accuracy of pH meter and involves practical problems of, for example, inability to deal with many samples, and the like.

(c) The pH-indicator colorimetric method, unlike the pH meter method, comprises using acetylcholine as a synthetic substrate, and measuring a pH change due to acetic acid produced by ChE in terms of the molecular absorbance of the indicator. As the indicator, there are used phenol red [Hiroshi Takahashi and Susumu Shibata, IGAKU-TO-SEIBUTSUGAKU (Medicine and Biology), 20, 96, (1959)], bromothymol blue [H. G. Biggs, et al., Amer. J. Clin. Path., 30, 181, (1958)], m-nitrophenol [Tadahide Sasaki, RINSHO-BYORI (Clinical Pathology), 12, 555, (1964)], etc. This method comprises simple operations and can deal with many samples, but it is pointed out that this method is disadvantageous, for example, in that the reaction time is long and in that during the reaction, the pH is not constant and is not sufficiently reproducible at low and high values.

All of the above-mentioned methods (a) to (c) use acetylcholine as a substrate, and in the case of such methods, the substrate itself also is disadvantageous because acetylcholine tends to undergo nonenzymatic hydrolysis and has no sufficient substrate specificity.

(d) The thiocholine method [P. Garry, J. Clin. Chem., 11 (2), 91 (1965)] uses acetylthiocholine, propylthiocholine, butylthiocholine or the like as a substrate. These substrates yields thiocholine by the enzymatic reaction of ChE, and this thiocholine reacts with 5,5'-dithiobis-2-nitrobenzoic acid (DTNB) to produce a yellow color. The thiocholine method comprises measuring this yellow color by means of a colorimeter. This method is advantageous, for example, in that it is excellent in reactivity, has a high sensitivity, comprises simple operations, can deal with many samples, and makes it possible to carry out the determination also by an initial velocity method. However, it is seriously affected by bilirubin in serum because of the yellow coloration and unavoidably affected by compounds having a thiol group such as glutathione. Furthermore, it is disadvantageous, for example, in that the instability of the substrate itself is a problem. These disadvantages are responsible for errors of determined values.

(e) The enzymatic method comprises using benzoylcholine [Hiroaki Okabe et al., RINSHO-BYORI (Clinical Pathology), 25, 751, (1977)], orthotoluoylcholine [Japanese Patent Application Kokai (Laid-Open) No. 138533/79] or the like as a substrate, converting choline produced by the enzymatic action of ChE into betaine by cholineoxidase, and subjecting 4-aminoantipyrine to oxidative condensation reaction with phenol or the like by thus produced hydrogen peroxide in the presence peroxidase to cause color production. In this method, since the coloration is red, there is not interference by bilirubin in serum, and many samples can be dealt with. However, since phenol or 4-aminoantipyrine used as a reagent for the color-producing system competitively inhibits ChE, the amount of these reagents used is greatly limited, so that sufficient color production is difficult. In general, a determination method via hydrogen peroxide is unavoidably affected not only by bilirubin in serum, reducing substances such as ascorbic acid and the like, etc. but also by choline produced by decomposition of phospholipids or the like. In particular, the employment of benzoylcholine as a substrate involves various problems, for example, its nonenzymatic hydrolyzability which causes troubles.

(f) The UV method includes various kinds of methods, and one of them is a method of W. Kalow using benzoylcholine as a substrate [W. Kalow and K. Genet, Can. J. Biochem. & Physical., 35, 339 (1957)], while another is a method using p-hydroxybenzoyl choline [Japanese Patent Application Kokai (Laid-Open) Nos. 110198/82 and 129999/83] as a substrate. The former comprises following a decrease in amount of the substrate caused by its hydrolysis by the enzymatic action of ChE at a determination wave length of 240 nm, measuring the change in absorbance per definite time, and thereby determining ChE activity. The principle of determination of this method is simple and plain because the decrease of the substrate is directly determined. However, this method is disadvantageous, for example, in that since the determination wave length is 240 nm, interference by serum components tends to occur, that since benzoylcholine, i.e., the substrate causes substrate inhibition, the substrate concentration of the reaction solution is limited, resulting in a narrow range of linearity, and that since nonenzymatic hydrolysis of benzoylcholine tends to occur, the reaction can not be carried out in the optimum pH range of ChE. It is disadvantageous also, for example, in that since the determination wave length is 240 nm, the determination is carried out on the slope of absorption spectrum, resulting in a large deviation of absorption coefficient due to the deviation of wave length.

The latter comprises using p-phydroxybenzoylcholine as a substrate, reacting p-hydroxybenzoate hydroxylase with p-hydroxybenzoic acid produced by the enzymatic action of ChE, in the presence of the coenzyme NADPH, and determining and following, at a wave length of 340 nm, a decrease of absorbance at the time of oxidation of NADPH into NADP by this reaction. This method is an excellent method for determining ChE activity which makes it possible to carry out the reaction at an almost optimum pH, permits removal of the defects of the hydrogen peroxide color-producing system, namely, influence of bilirubin, reducing substances such as ascorbic acid and the like, etc. and interference by choline produced by decomposition of phospholipids, is free from the defects of the thiocholine method, and is suitable for an autoanalyzer capable of dealing with many samples. However, since NADPH, the coenzyme used, is an expensive reagent and is poor in stability, it is difficult to control while being kept at a definite quality. Further, in this method, p-hydroxybenzoate hydroxylase, protocatechuate 3,4-dioxygenase or the like is used as a reagent enzyme in the determination and moreover the principle of determination is considerably complicated as compared with the former determination method; therefore there are many factors which produce an error of the resulting determined value.

Further another example of the UV method is a method using 3,4-dihydroxybenzoylcholine iodide as a synthetic substrate (European Patent Publication No. 0160980). This method is a very excellent method for determining ChE activity which makes it possible to carry out the reaction in the optimum pH range of ChE, and is free from interference by other components in serum. In this method, the rate of the decrease of the substrate due to hydrolysis of said substrate by enzyme action of ChE is measured at a wave length of 340 to 360 nm, and in this wave length range, the measuring of the absorbance is carried out at the portion of the slope of absorption spectrum, so that an error of the resulting determined value tends to be produced depending on the kind of measuring instrument, etc. Therefore, this method admits of some improvement in the interchangeability of apparatus when the determination is carried out by means of an ordinary apparatus selected in a wide range.

On the other hand, as cholinesterases, there are known two kinds, namely, pseudo-cholinesterase existing in serum and true-cholinesterase existing in erythrocyte. Further, the pseudo-cholinesterase includes two kinds thereof, i.e., abnormal pseudo-cholinesterase and normal pseudo-cholinesterase. Cholinesterase whose activity is usually determined in a clinical examination is pseudo-cholinesterase in serum, but since serum is contaminated with true-cholinesterase in some cases, a substrate which reacts selectively with pseudo-cholinesterase alone is preferable as a synthesized substrate used in a method for determining ChE. As to a method for determining ChE activity, determination of abnormal pseudo-cholinesterase activity is also important. For determining abnormal pseudo-cholinesterase, there can be employed, for example, the above-mentioned UV method using p-hydroxybenzoylcholine. In this case, sodium fluoride is used in some cases in carrying out the determination. When sodium fluoride is used, the method using p-hydroxybenzoylcholine is seriously affected by sodium fluoride and hence is not suitable for determining abnormal pseudo-cholinesterase activity.

As described above, the conventional methods for determining the enzymatic activity of ChE involve various problems, and therefore it is desired to develop a method for determining ChE activity which has advantages such as no error in the determined value, good reproducibility of the determined value, and high substrate specificity for pseudo-cholinesterase.

SUMMARY OF THE INVENTION

We have devoted ourselves to research in order to remove the defects of the conventional methods and have accomplished this invention. In other words, as a result of investigation on the determination of ChE activity by a UV method using, as a substrate, 2,3-dihydroxybenzoylcholine iodide (hereinafter referred to a Compound I) or 3,5-dihydroxybenzoylcholine iodide (hereinafter referred to as Compound II) which are two compounds of the general formula (I), we have found the following facts. A wave length of about 340 to about 360 nm can be used as the determination wave length, and in this case, interference by serum components other than ChE hardly occurs. Compounds I and II are very stable to nonenzymatic hydrolysis and react specifically with ChE in serum, in particular, pseudo-cholinesterase, and therefore the employment of Compound I or II permit very accurate and highly reproducible determination of ChE activity in serum which has also other various advantages. Based on the above finding, this invention has been accomplished.

That is to say, this invention is a method for determining cholinesterase activity, characterized by using a choline derivative of the general formula (I) as a substrate, more particularly a method for determining cholinesterase activity which comprises mixing a sample containing cholinesterase with a choline derivative of the general formula (I), then measuring the optical absorbance of the resulting mixture at a wave length in the ultraviolet region, and thereby determining cholinesterase activity.

DETAILED DESCRIPTION OF PREFERRED EMBODIMENTS

Compounds I and II of this invention are well known (Journal of Chromatography, 260 (1983) 193–199). In the formula I, X is a halogen atom such as iodine, chlorine, bromine or fluorine. Compound I can be obtained, for example, by preparing 3,5-dibenzyloxybenzoic chloride from 3,5-dihydroxybenzoic acid, reacting the same with dimethylaminoethanol, removing the protecting group, and then reacting the resulting compound with methyl iodide. Compound II can be obtained in the same manner as for Compound (I).

Figure 1:
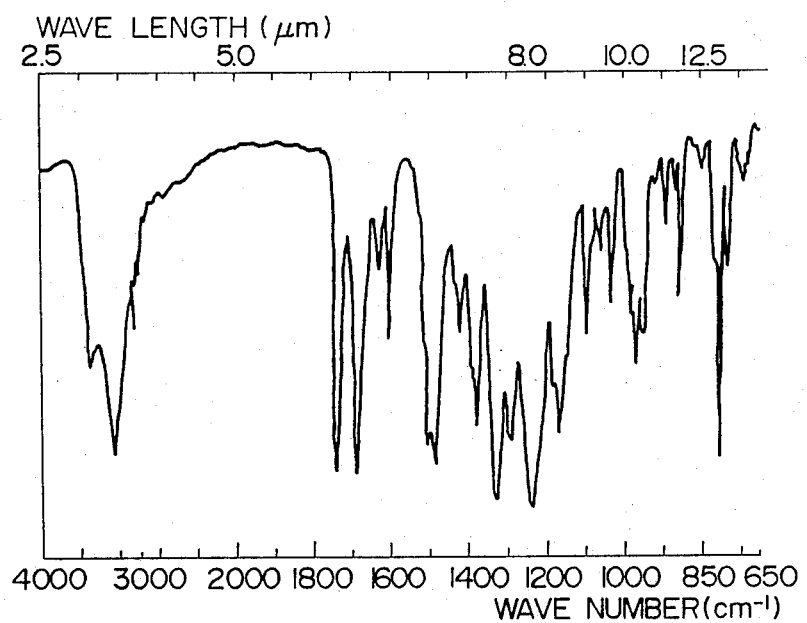
FIG. 1 shows an IR spectrum of 2,3-dihydroxybenzoylcholine iodide.
Figure 2:
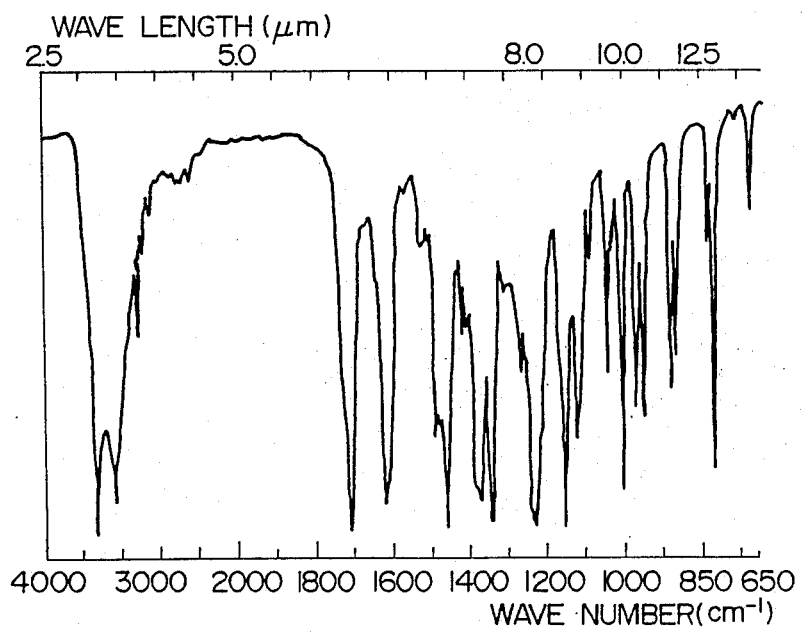
FIG. 2 shows an IR spectrum of 3,5-dihydroxybenzoylcholine iodide.
Figure 3:
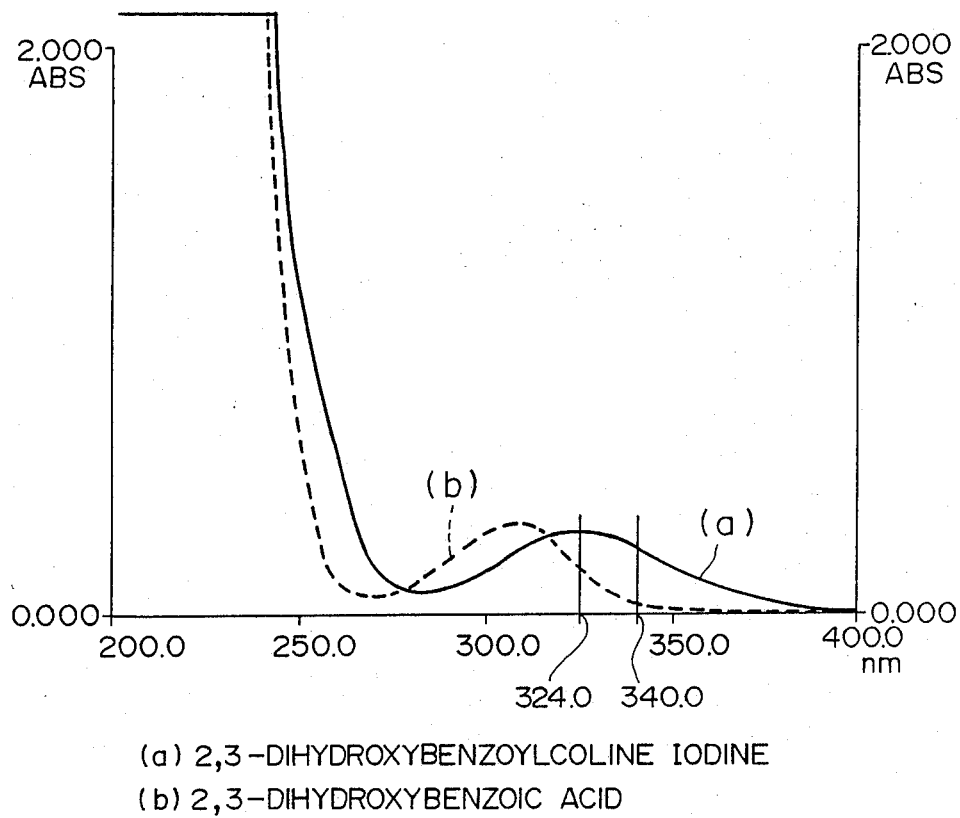
FIG. 3 shows UV spectra of 2,3-dihydroxybenzoylcholine iodide (a) (concentration: 100 μM) and 2,3-dihydroxybenzoic acid (b) (concentration: 100 μM) measured in a 200 mM glycylglycine buffer solution (pH 8.20).
Figure 4:
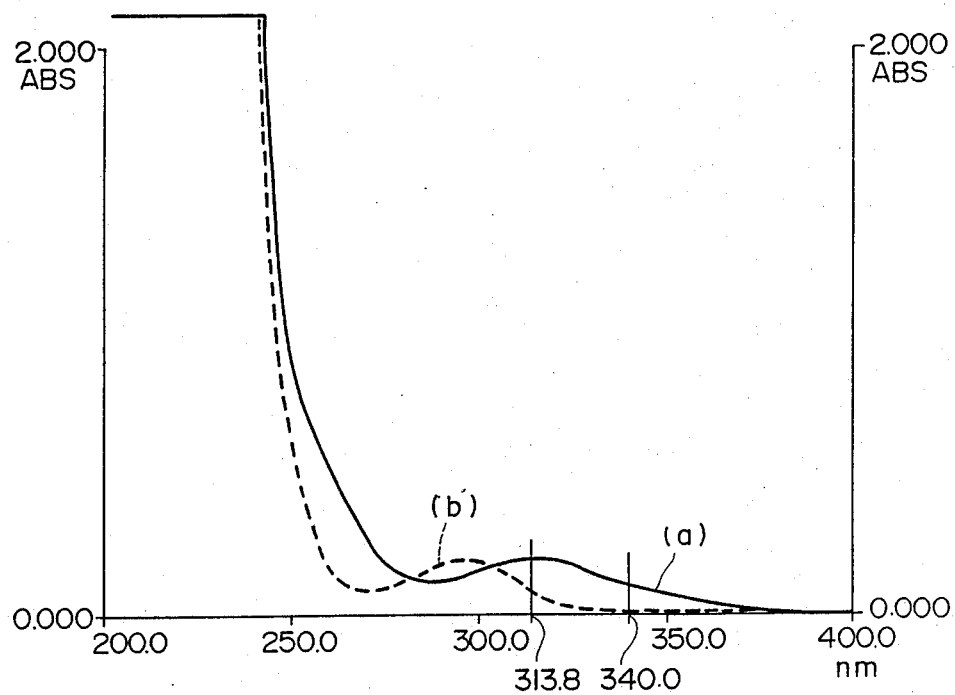
FIG. 4 shows UV spectra of 3,5-dihydroxybenzoylcholine iodide (a) (concentration: 100 μM) and 3,5-dihydroxybenzoic acid (b) (concentration: 100 μM) measured in a 200 mM glycylglycine buffer solution (pH 8.60).

UV spectra of Compound I and 2,3-dihydroxybenzoic acid are shown in FIG. 3, and those of Compound II and 3,5-dihydroxybenzoic acid in FIG. 4. On hydrolysis by the action of ChE, Compound I or II gives choline and 2,3-dihydroxybenzoic acid or 3,5-dihydroxybenzoic acid, respectively. Choline has no UV absorption at a wave length longer than 300 nm. 2,3-Dihydroxybenzoic acid and 3,5-dihydroxybenzoic acid have almost no UV absorption at a wave length longer than 340 nm. On the other hand, Compound I has UV absorption at a wave length shorter than 370 nm, and Compound II at a wave length shorter than 360 nm. Therefore, when Compound I or II is used as a substrate for determining ChE activity and the reaction is followed at a determination wave length of preferably about 340 to about 370 nm, a decrease in amount of the substrate Compound I or II can accurately be followed. In the above-mentioned UV method of W. Kalow, the determination wave length is 240 nm and hence serious interference by blood components occurs in initial absorptions. On the other hand, no serious interference occurs at the determination wave length of 340 to 360 nm for the substrates of this invention, so that it is easy to determine the optimum determination conditions. The two substrates are stable to nonenzymatic hydrolysis. For example, hydrolysis hardly occurred under the conditions of 37° C. in 200 mM glycylglycine buffer solution having a pH of 8.20 for 10 minutes (see FIG. 7).

This result indicates that nonenzymatic hydrolysis is negligible in the determination. In determining ChE activity, as a buffer for keeping the pH constant, there can be used barbiturates, phosphates, pyrophosphates, glycine, glycylglycine, tris(hydroxymethyl)aminomethane, etc. Any buffer other than those described above can be used so long as it can retain its buffer capacity in the pH range from 7.5 to 10.0.

The Michaelis constants (Km values) of Compounds I and II for ChE are substantially the same as that of benzoylcholine and are $3.33 \times 10^{-5}$ mol/liter in a 200 mM glycylglycine buffer solution (pH 8.20) for Compound I and $1.25 \times 10^{-4}$ mol/liter in a 200 mM glycylglycine buffer solution (pH 8.60) for Compound II. Since the Km values of Compounds I and II are sufficiently small, their affinity for ChE are high. Therefore, the reaction can be carried out at sufficient substrate concentration in the reaction system of the determination method of this invention, and the period during which the change in absorbance per definite time is constant (the range of linearity with the lapse of time) is enlarged, so that the determination can sufficiently be carried out for a high unit of the activity.

When Compound I or II is used as a substrate, the optimum pH of ChE is 8.00 to 8.60 in a 200 mM glycylglycine buffer solution. For example, it was pH 8.20 to 8.40 for Compound I (see FIG. 6). As described above, Compounds I and II are stable to noenzymatic hydrolysis at pH 8.20, and hence the determination method of this invention makes it possible to carry out the reaction at the optimum pH of ChE.

Figure 15:
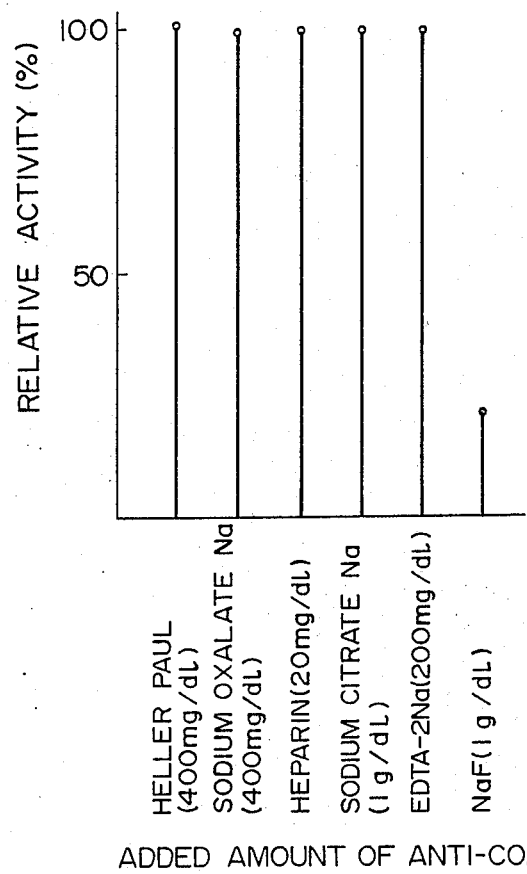

It is as described above that when the coexisting substances in sample affect the resulting determined value, they cause an error of the determined value. The determination method of this invention is hardly affected by the coexisting substances also from the viewpoint of its principle. Coexxisting substances, for example, up to 20 mg/dl of ascorbic acid, up to mg/dl of uric acid, up to 500 mg/dl of glucose, up to 200 mg/dl of hemoglobin, up to 5 g/dl of albumin, up to 20 mg/dl of bilirubin, up to 50 mg/dl of glutatione (reduced form) caused no trouble in addition tests (see FIGS. 8 to 14). Further, no trouble was caused also in addition tests on EDTA·2Na, citrate, heparin, oxalate, dihydrogenoxalic acid, and the like as anti-coagulants (see FIG. 15).

In the above-mentioned UV method of W. Kalow, benzoylcholine, the substrate used therein, has an absorption maximum near 230 nm in a 1/15M phosphate buffer (pH 7.40), and the absorption curve slopes at the determination wave length of 240 nm. Therefore, as shown in Table 1, the deviation of absorption coefficient due to the deviation of wave length is large. In the case of the substrate benzoylcholine, a deviation of the determination wave length of ±2 nm from 240 nm results in a deviation of the absorption coefficient of about 15%. In the case of the novel substrates of this invention the deviation of absorption coefficient is small. For example, a deviation of ±2 nm from the determination wave length of 340 nm results in a deviation of absorption coefficient of about 6% for Compound I or about 4% for Compound II, which are much smaller than that caused in the UV method of W. Kalow. This suggests that the difference in absorption coefficient caused by the problem of low accuracy of wave length of analyzer, etc. becomes very small. This invention is a determination method which is very unsusceptible to influence of the coexisting substances in a sample, and in which causes of error in the resulting determined value are greatly removed by virtue of not only the above-mentioned unsusceptibility but also the fact that the difference in absorption coefficient resulting from the low accuracy of wave length of analyzer, etc. is much smaller than that caused in the UV method of W. Kallow.

(1) The reaction mechanism of the determination system is simple and plain, and there are very few causes of error in the determined value.
(2) Since Compounds I and II used as substrates are stable to nonenzymatic hydrolysis and oxidation, the reproducibility of the determined value is very good.

TABLE 1

Deviation of absorption coefficient of substrate solution due to deviation of wave length
(measured by means a HITACHI 220-A)

| Wave length (nm) | Temperature (°C.) | Substrate | Buffer solution | $\epsilon$ $(l \cdot mol^{-1} \cdot cm^{-1})$ | Deviation due to deviation of wave length (%) $\pm 2$ nm | $\pm 5$ nm |
|---|---|---|---|---|---|---|
| 240 | |  | 1/15 phosphate pH 7.40 (25° C.) | 9,655 | 82.8–113.6 | 57.0–126.1 |
| | 37 | Compound I | 200 mM glycyl-glycine pH 8.20 (25° C.) | 2,458 | 93.3–106.8 | 83.4–115.9 |
| 340 | | Compound II | 200 mM glycyl-glycine pH 8.60 (25° C.) | 1,795 | 96.4–103.8 | 89.4–109.1 |

The Compounds I and II used in the method of this invention are substrates having a very high specificity which react well specifically with pseudo-cholinesterase existing in serum among cholinesterases but hardly react with true-cholinesterase existing in erythrocyte. Therefore, they are very suitable as substrates for determining ChE activity.

On the other hand, in the fields of surgery and psychiatry, an examination for abnormal pseudo-cholinesterase is important from the viewpoint of the relationship between anesthetics and pseudo-cholinesterase. That is to say, since a person having atypical forms of human serum cholinesterase meets death from shock, or the like at the time of anethesia in some cases, it is important to determine abnormal pseudo-cholinesterase activity before anethesia. The determination method of this invention is simple and plain with regard to the reaction mechanism and hence is very suitable also as a method of examination for abnormal pseudo-cholinsterase.

Embodiments of the method for determining ChE activity of this invention are shown in the examples described hereinafter, and the procedures of a conventional UV method can be employed therein. That is to say, ChE activity can be determined, for example, by adding a sample containing cholinesterase to a buffer solution, adding thereto Compound I or an aqueous solution containing Compound I, stirring the resulting mixture, irradiating the mixture with light having a wave length in the UV range, and measuring the change of optical absorbance with the lapse of time ($\Delta$O.D.). For such determination, there is preferably used a kit consisting essentially of a buffer solution and a substrate solution containing Compound I or II. The kit may include additional materials which do not materially affect the basic and characteristics of the invention.

The method for determining ChE activity of this invention is, as described above, free from the various problems of the conventional methods. The advantages of this invention are as described below.

(3) Compounds I and II have a high substrate specificity for pseudo-cholinesterase.
(4) Since none of enzymes and coenzymes for redox systems and reagents for coloration systems are used in addition to the substrate, the method of this invention is inexpensive.
(5) As described above, said method is hardly affected by sample components such as bilirubin, ascorbic acid, glutathione and the like and anticoagulants.
(6) Since the substrate is stable, the reaction can be carried out at the optimum pH (8.00 to 8.60) for ChE.
(7) It is unnecessary to employ a sample blank for each sample. Therefore, the determination can be carried out easily and rapidly, so that many samples can be dealt with.
(8) Examination for abnormal pseudo-cholinesterase is possible.
(9) The determination is possible up to a high unit of the activity.
(10) The deviation of absorption coefficient due to the deviation of wave length is smaller than that caused in the UV method of W. Kalow, and it is possible to reduce the difference in absorption coefficient resulting from the low accuracy of wave length of analyzer.

As described above, the method for determining ChE activity of this invention is free from the defects of the conventional methods, has many advantages and characteristics, permits accurate and simple determination of ChE activity, and can significantly contribute to determination of ChE activity in daily clinical examinations.

Accordingly, the method for determining ChE activity of this invention is very useful as a method for determining the ChE activity in serum of normal persons, patients with liver disease, patients with kidney disease, etc.

This invention is further explained below in more detail with reference to Referential Example and Examples, which are not by way of limitation but by way of illustration.

REFERENTIAL EXAMPLE

Synthesis process of 2,3-dihydroxybenzoylcholine iodide (Compound I) and 3,5-dihydroxybenzoylcholine iodide (Compound II).

A solution of 12.3 g of 2,3-dihydroxybenzoic acid in 40 ml of methanol containing 2.4 ml of concentrated sulfuric acid was refluxed on an oil bath for 10 minutes, after which the solvent was distilled off under reduced pressure and ether was added to the oily residue. The resulting mixture was washed with a saturated aqueous sodium chloride solution, and the ether phase was dried over anhydrous magnesium sulfate. Then, the solvent was distilled off under reduced pressure to obtain 11.8 g of a crystalline residue. This residue was recrystallized from ether/n-hexane to obtain 10.7 g of methyl 2,3-dihydroxybenzoate. To 10 g of the methyl 2,3-dihydroxybenzoate were added 25.1 g of anhydrous potassium carbonate and 16.5 ml of benzyl chloride, and the resulting mixture was subjected to reaction in 26.0 ml of DMF on an oil bath at 150° to 160° for 30 minutes while preventing moisture. After completion of the reaction, the reaction mixture was added to 160 ml of cold water, and the crystals thus formed were collected by filtration and sufficiently washed with water to obtain 20.7 g of crystals (methyl 2,3-dibenzyloxybenzoate). These crystals were dissolved in a methanolic sodium hydroxide solution prepared from 4.4 g of sodium hydroxide, 2.2 ml of water and 88 ml of methanol, and the resulting solution was refluxed on a water bath for 30 minutes. To the reaction solution was added 80 ml of warm water, and the resulting solution was adjusted to pH 2 with cold 5N HCl, after which the crystals thus deposited was collected by filtration and dried in vacuo over phosphorus pentaoxide to obtain 17.0 g of crystals. In 25 ml of dried benzene were dissolved 6.7 g of these crystals (2,3-dibenzyloxybenzoic acid), followed by adding thereto 1.8 ml of thionyl chloride and several drops of pyridine, and the resulting mixture was refluxed on a water bath for 40 minutes. After completion of the reaction, the reaction mixture was cooled and n-hexane was added, and the crystals thus deposited were collected by filtration and dried in vacuo over phosphorus pentaoxide to obtain 3 g of crystals (2,3-dibenzyloxybenzoic chloride). A solution of 3 g of these crystals dissolved in 6 ml of benzene was added dropwise to a solution of 1 ml of dimethylaminoethanol dissolved in 16 ml of benzene, with cooling to 5° to 10° C. After the addition, the resulting mixture was stirred overnight at room temperature to be subjected to reaction, and subsequently washed with water and then a saturated aqueous sodium chloride solution. The benzene phase was dried over anhydrous magnesium sulfate, and then the solvent was distilled off under reduced pressure to obtain 1.9 g of an oily substance (2-(dimethylamino)ethyl 2,3-dibenzyloxybenzoate). This substance was dissolved in 260 ml of ethanol, followed by adding thereto 1 g of palladium black, and catalytic reduction was carried out for 5 hours, after which the catalyst was filtered off and the ethanol was distilled off under reduced pressure to obtain 0.9 g of an oily substance (2-(dimethylamino)ethyl 2,3-dihydroxybenzoate). This substance was dissolved in 9 ml of acetone, followed by adding thereto 0.6 g of methyl iodide, and the resulting mixture was allowed to stand overnight at room temperature to deposit crystals. The crystals were collected by filtration, sufficiently washed with acetone, and then dried overnight in vacuo over phosphorus pentaoxide to obtain 0.85 g of 2,3-dihydroxybenzoylcholine iodide, m.p. 208°-210° C. These crystals gave a single spot (Rf=0.34) in a silica gel thin layer chromatography (n-butanol:acetic acid:water=4:1:2).

Elementary analysis values: for $C_{12}H_{18}NO_4I$ (M.W. 367.166): Found (%): C: 39.7; H: 5.07; N: 3.90 Calculated (%): C: 39.25; H: 4.94; N: 3.81.

3,5-Dihydroxybenzoylcholine iodide was synthesized in the same manner as described above. M.p. 208°-210° C. These crystals gave a single spot (Rf=0.38) in a silica gel thin layer chromatography (n-butanol:acetic acid:water=4:1:2).

Elementary analysis values: for $C_{12}H_{18}NO_4I$ (M.W 367.166): Found (%): C: 39.11; H: 5.05; N: 3.88 Calculated (%): C: 39.25; H: 4.94; N: 3.81.

IR spectra and UV spectra of the two products synthesized are individually shown in FIGS. 1 to 4.

EXAMPLE 1

(1) a 200 mM glycylglycine buffer solution (pH 8.20, 25° C.)

(2) a sample (3) a 2.0 mM aqueous substrate (Compound I) solution

To the 2.0 ml of the buffer solution of (1) was added 0.025 ml of the sample, and preheating was conducted at 37° for about 2 to 10 minutes. Thereto was added 0.5 ml of the substrate solution of (3) and the resulting mixture was quickly stirred and then subjected to determination by means of a spectroscope, whereby the change per minute of optical absorbance ($\Delta$.O.D.) was measured. The optical absorbance at 340 nm of the substrate was determined and followed with the lapse of time. The pH of the glycylglycine buffer solution was adjusted at 25° C. As the serum, CONSERA I (lyophilized pooled serum for accuracy control; mfd. by Nissui Pharmaceutical Co., Ltd.), was used and the serum was diluted with a 0.877% aqueous sodium chloride solution containing 5% albumin.

Figure 5:
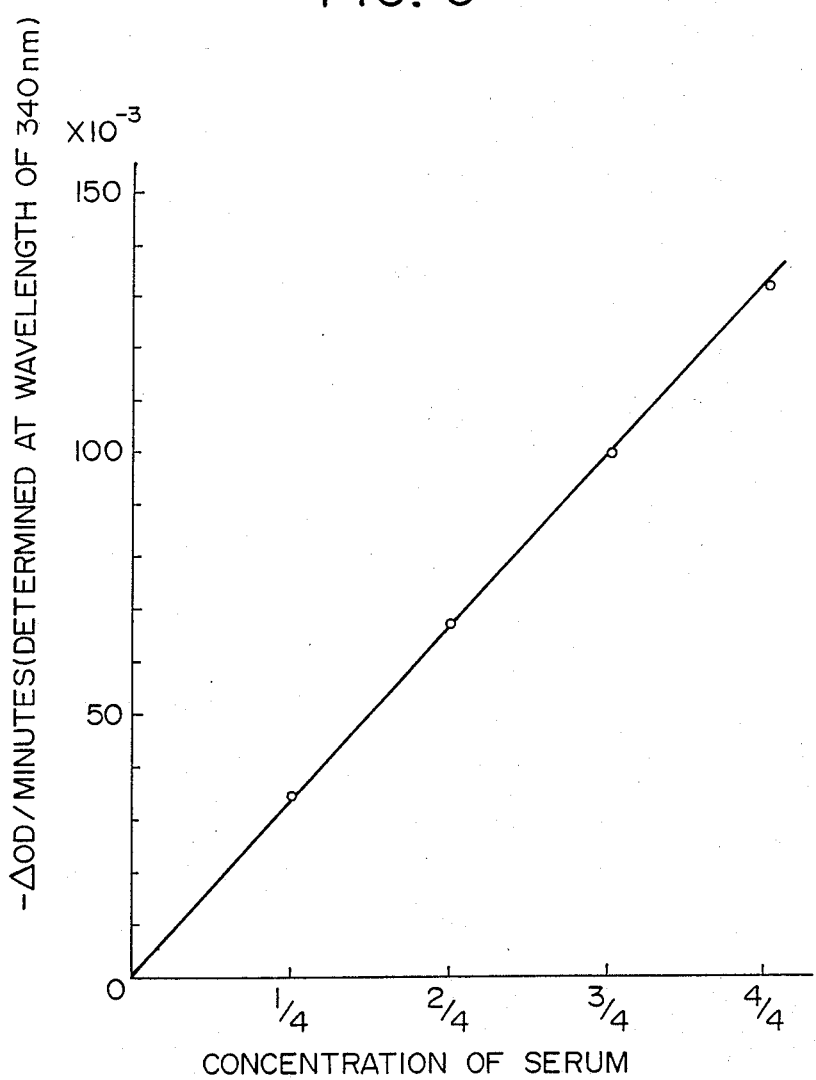
FIG. 5 is a graph showing the relationship between serum dilution and ΔO.D.

The relationship between dilution of serum and $\Delta$O.D. is shown in FIG. 5. The results obtained showed a perfectly straight line passing through the origin. This fact indicates that the ChE activity and $\Delta$O.D. are proportional to each other, and that said novel method for determining ChE activity is practical and useful.

EXAMPLE 2

Figure 6:
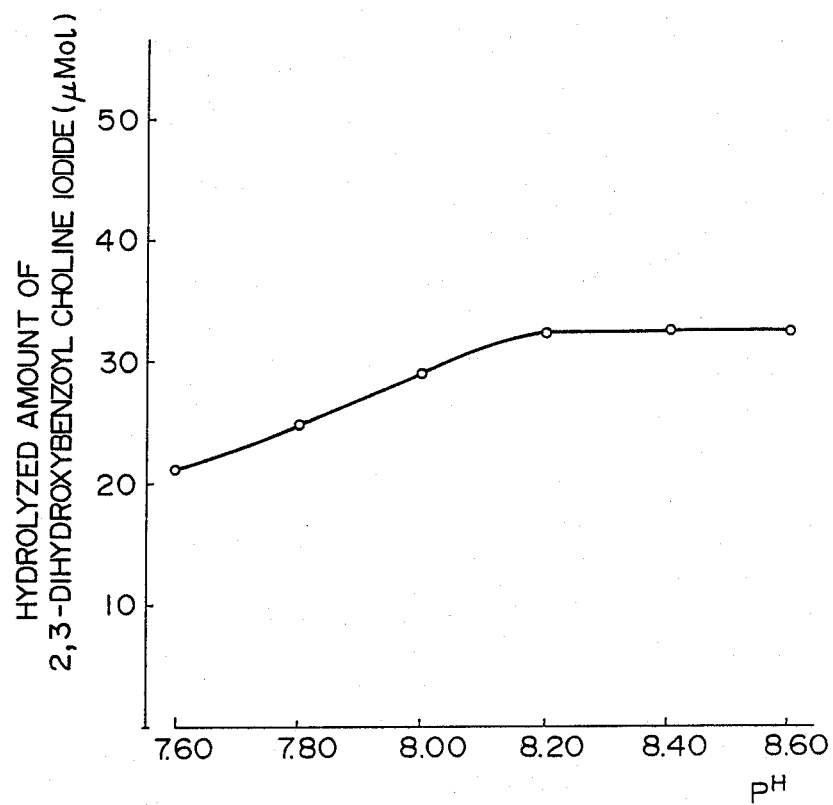
FIG. 6 is a graph showing the optimum pH of ChE.

The pH of the buffer solution of (1) in Example 1 was varied from 7.60 to 8.60 and the optimum pH for ChE in said method was determined. The same determination as in Example 1 was carried out except for changing the pH of the buffer solution, whereby ChE activity at each pH was determined. From the determined value, the hydrolyzed amount ($\mu$mol) of Compound I with ChE was calculated. The results obtained are shown in FIG. 6. Under these conditions, the optimum pH was 8.20 to 8.60.

EXAMPLE 3

Figure 7:
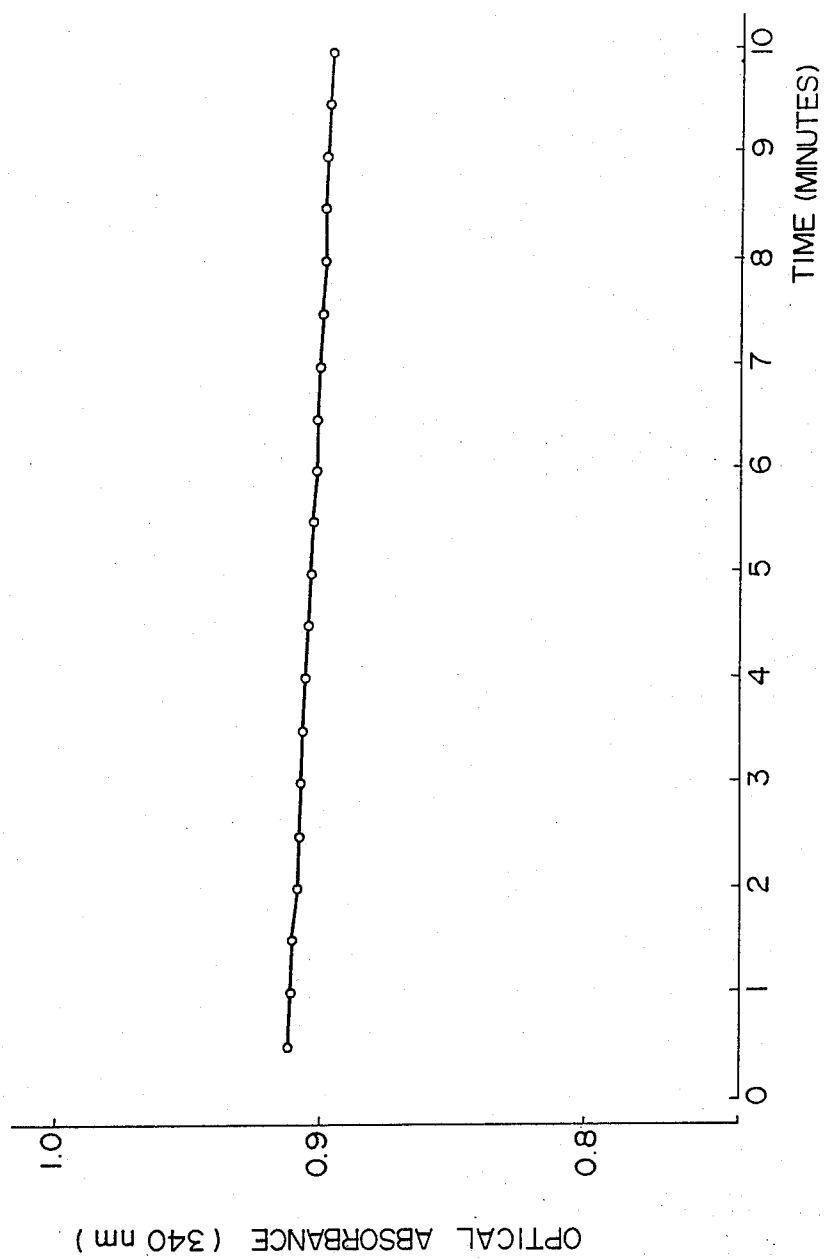
FIG. 7 is a graph showing the stability of 2,3-dihydroxybenzoylcholine iodide to nonenzymatic hydrolysis.
Figure 8:
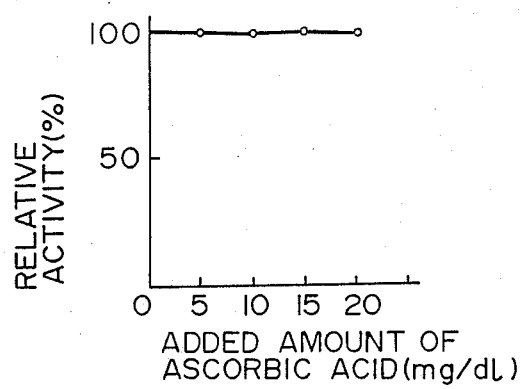
FIGS. 8 to 15 are graphs showing the influences of additives.
Figure 9:
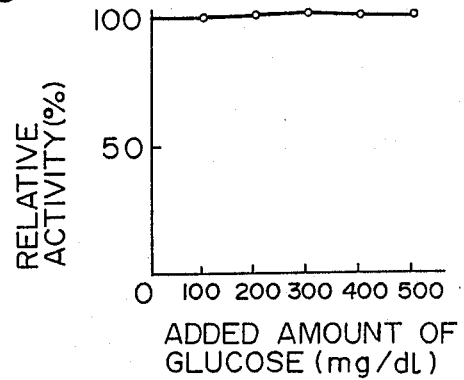
Figure 10:
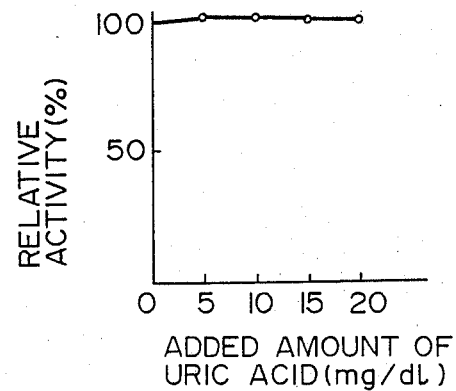
Figure 11:
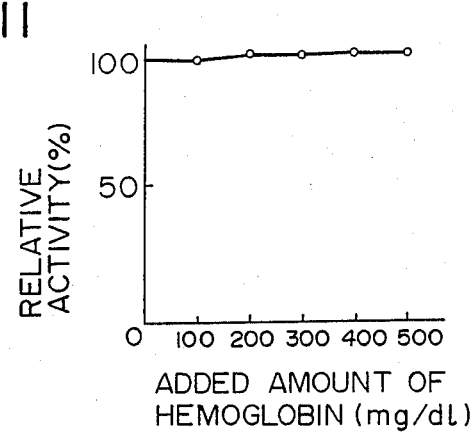
Figure 12:
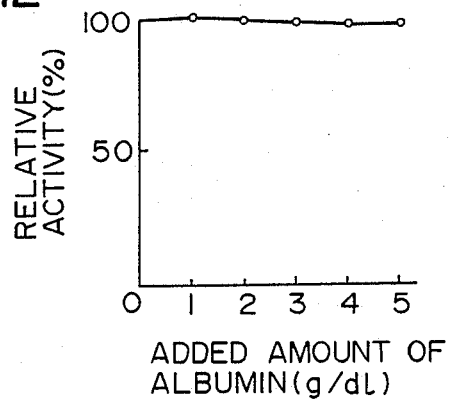
Figure 13:
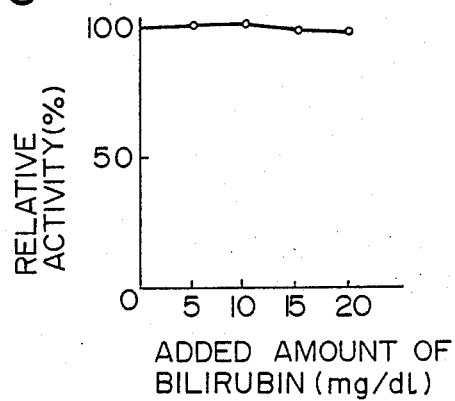
Figure 14:
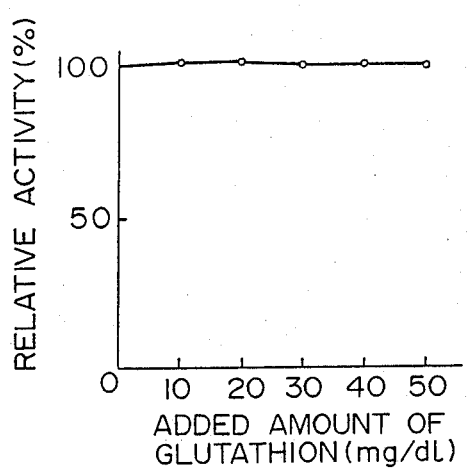

To 2.0 ml of the buffer solution of (1) in Example 1 (pH 8.20) was added 0.5 ml of the substrate solution of (3), and the resulting solution was placed in a heat insulating cuvette having a temperature of 37° C. The change of optical absorbance at a wave length of 340 nm was followed with the lapse of time, whereby the stability of the substrate to nonenzymatic hydrolysis was examined. As a result, the substrate was almost stable up to 10 minutes as shown in FIG. 7. Since the substrate Compound I is stable at the optimum pH of 8.20, it is unnecessary to measure a reagent blank value for each sample.

EXAMPLE 4

The influence of the following additives in the reaction system was examined by adding each of the additives and determining ChE activity according to the determination method in Example 1.

| | Additive | Added amount |
|---|---|---|
| (1) | Ascorbic acid | 0-20 mg/dl |
| (2) | Glucose | 0-500 mg/dl |
| (3) | Uric acid | 0-20 mg/dl |
| (4) | Hemoglobin | 0-500 mg/dl |
| (5) | Albumin | 0-5 g/dl |
| (6) | Bilirubin | 0-20 mg/dl |
| (7) | Glutathione | 0-50 mg/dl |
| (8) | Anti-coagulant | |
| | Heller paul (a mixture of potassium oxalate with ammonium oxalate) | 400 mg/dl |
| | Sodium oxalate | 400 mg/dl |
| | Heparin | 20 mg/dl |
| | Sodium citrate | 1 g/dl |
| | EDTA.2Na | 200 mg/dl |
| | NaF | 1 g/dl |

The determination results are shown in terms of relative activity (the percentage of activity based on the ChE activity value determined without adding any additive) (%). Since NaF used as an anti-coagulant acts also as an inhibitor of psendo-cholinesterase, determination of ChE activity by any method generally gives no accurate determined value in the presence of NaF. Therefore, from the result for NaF in FIG. 15, NaF cannot be used as an anti-coagulant in determining pseudo-cholinesterase activity.

EXAMPLE 5

Method for determining serum ChE activity

The determination was carried out on the following sera:

| (1) serum I: | CONSERA I (X2) | 0.025 ml |
|---|---|---|
| (2) serum II: | CONSERA I | 0.025 ml |
| (3) serum III: | (Control serum: mfd. by Boehringer Maunheim) | 0.025 ml |

The sera were diluted with a 0.877% aqueous sodium chloride solution containing 5% albumin.

The ChE activity value is calculated from the following equation.

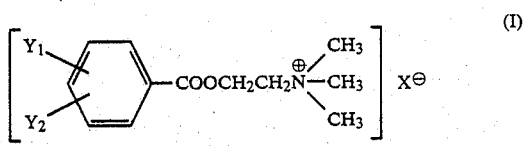

$^{(1)}\Delta O.D.$ is a change per minute of optical absorbance at a determination wave length of 340 nm.
$^{(2)}$The molecular absorption coefficient at 340 nm is 2458.

Figure 16:
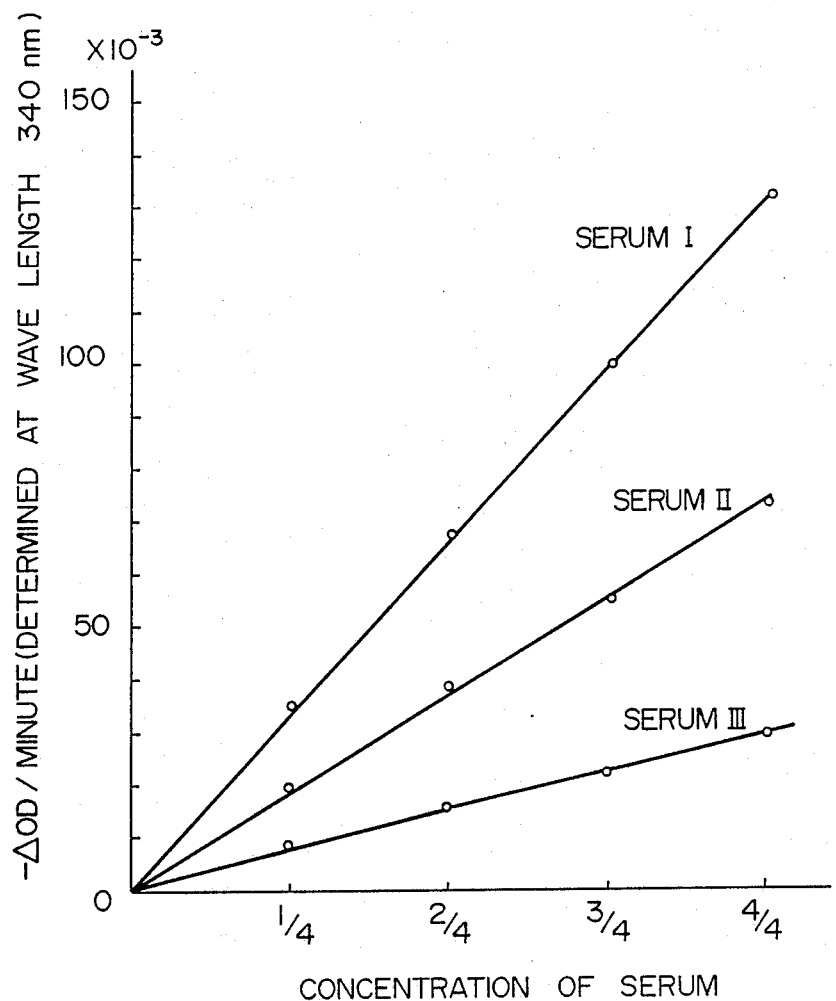
FIG. 16 is a graph showing the relationships between serum dilution and enzymatic activity observed for three kinds of sera.

As shown in FIG. 16, for all of the three sera, the serum dilution and the enzyme activity are proportional to each other in the manner of a straight chain passing through the origin very sufficiently.

What is claimed is:

1. A method for determining pseudocholinesterase activity in a sample containing pseudocholinesterase as one of cholinesterases which comprises admixing said sample with a substrate, a choline derivative represented by the general formula (I):

$$\left[ Y_1 \underset{Y_2}{\diagdown} \hspace{-0.5em} \bigcirc \hspace{-0.5em} -COOCH_2CH_2\overset{\oplus}{N} \underset{CH_3}{\overset{CH_3}{\diagup}} CH_3 \right] X^{\ominus} \quad (I)$$

wherein X is a halogen atom; $Y_1$ is a hydroxyl group as a substituent in the 2- or 5- position; and $Y_2$ is a hydroxyl group as a substituent in the 3-position; and measuring the optical absorbance of the reaction product of the admixture to determine the pseudocholinesterase activity.

2. The method for determining pseudocholinesterase activity according to claim 1, which comprises measuring the optical absorbance at a wave length in the ultraviolet region.

3. The method for determining pseudocholinesterase activity according to claim 2, wherein the optical absorbance at a wave length of about 340 to about 370 nm is measured.

4. The method for determining pseudocholinesterase activity according to claim 2, wherein the determination is carried out while maintaining the pH at 8.00 to 8.60 by use of a buffer.

5. The method for determining pseudocholinesterase activity according to claim 4, wherein the buffer is selected from the group consisting of barbiturates, phosphates, pyrophosphates, glycine, glycylglycine, and tris(hydroxymethyl)aminomethane.

6. The method for determining pseudocholinesterase activity according to claim 2, wherein the choline derivative is 2,3-dihydroxybenzoylcholine iodide or 3,5-dihydroxybenzoylcholine iodide.

* * * * *